United States Patent
Maki et al.

(10) Patent No.: US 11,807,612 B2
(45) Date of Patent: Nov. 7, 2023

(54) HETEROCYCLIC COMPOUND AND SALT THEREOF, AND LUMINESCENT SUBSTRATE COMPOSITION

(71) Applicants: The University of Electro-Communications, Chofu (JP); TOKYO UNIVERSITY OF PHARMACY & LIFE SCIENCES, Hachioji (JP)

(72) Inventors: Shojiro Maki, Chofu (JP); Nobuo Kitada, Chofu (JP); Ryohei Moriya, Hachioji (JP); Hiroshi Aoyama, Hachioji (JP); Ryosuke Ijuin, Hachioji (JP)

(73) Assignees: The University of Electro-Communications, Chofu (JP); TOKYO UNIVERSITY OF PHARMACY & LIFE SCIENCES, Hachioji (JP)

( * ) Notice: Subject to any disclaimer, the term of this patent is extended or adjusted under 35 U.S.C. 154(b) by 0 days.

(21) Appl. No.: 17/999,931

(22) PCT Filed: Jun. 29, 2021

(86) PCT No.: PCT/JP2021/024620
§ 371 (c)(1),
(2) Date: Nov. 28, 2022

(87) PCT Pub. No.: WO2022/004744
PCT Pub. Date: Jan. 6, 2022

(65) Prior Publication Data
US 2023/0192635 A1 Jun. 22, 2023

(30) Foreign Application Priority Data
Jun. 29, 2020 (JP) ................... 2020-112102

(51) Int. Cl.
*C07D 277/56* (2006.01)
*C09K 11/06* (2006.01)

(52) U.S. Cl.
CPC ............ *C07D 277/56* (2013.01); *C09K 11/06* (2013.01); *C09K 2211/1018* (2013.01)

(58) Field of Classification Search
CPC .................................................. C07D 277/56
See application file for complete search history.

(56) References Cited

U.S. PATENT DOCUMENTS

2011/0033878 A1    2/2011    Maki et al.

FOREIGN PATENT DOCUMENTS

| JP | 2009184932 A | 8/2009 |
|---|---|---|
| JP | 2014082947 A | 5/2014 |
| JP | 2014218456 A | 11/2014 |
| JP | 2015193584 A | 11/2015 |

OTHER PUBLICATIONS

Li, et al. CN 112830950 (abstract), retrieved from STN; May 25, 2021. Accession No. 2021:1147932.*
Dec. 13, 2022, International Preliminary Report on Patentability issued in the International Patent Application No. PCT/JP2021/024620.
Jan. 17, 2023, Notification of Reasons for Refusal issued by the Japan Patent Office in the corresponding Japanese Patent Application No. 2022-534056.
Ryohei Saito et al., Synthesis and Luminescence Properties of Near-Infrared N-Heterocyclic Luciferin Analogues for In Vivo Optical Imaging, Bulletin of the Chemical Society of Japan, 2019, pp. 608-618, vol. 92, No. 3.
Satoshi Iwano et al., Single-cell bioluminescence imaging of deep tissue in freely moving animals, Science, Feb. 23, 2018, pp. 935-939, vol. 359, Issue 6378.
Sep. 7, 2021, International Search Report issued in the International Patent Application No. PCT/JP2021/024620.
Sep. 7, 2021, Written Opinion of the International Searching Authority issued in the International Patent 4pplication No. PCT/JP20211024620, along with its English translation, and Applicant's Remarks on Box No. VIII of the Written Opinion.

* cited by examiner

*Primary Examiner* — Shawquia Jackson
(74) *Attorney, Agent, or Firm* — KENJA IP LAW PC

(57) ABSTRACT

The aim is to provide a novel compound that can luminesce with high brightness and be used as a luminescent substrate in a firefly bioluminescence system. Provided is a heterocyclic compound, or salt thereof, represented by the following general formula (1):

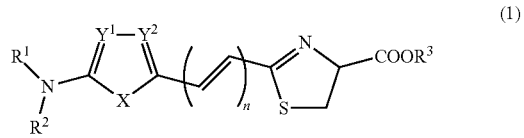

(1)

[$R^1$, $R^2$, and $R^3$ are independently hydrogen or an alkyl group having a carbon number of 1-4, with provisos that $R^1$ and $R^2$ are optionally bonded to form a ring and that one of $R^1$ and $R^2$ is optionally bonded to $Y^1$ to form a ring; X is S, O, $NR^4$, or $CH_2$, and $Y^1$ and $Y^2$ are independently N or $CR^4$, where each $R^4$ is independently hydrogen, an alkyl group having a carbon number of 1-4, an alkenyl group having a carbon number of 2-4, or an acyl group having a carbon number of 2-4; n is an integer of 0-4].

20 Claims, 1 Drawing Sheet

HETEROCYCLIC COMPOUND AND SALT THEREOF, AND LUMINESCENT SUBSTRATE COMPOSITION

TECHNICAL FIELD

The present disclosure relates to a novel heterocyclic compound and salt thereof and also to a luminescent substrate composition.

BACKGROUND

Visualization of deep tissue is a significant challenge in the field of life sciences. There is ongoing research in which bioluminescence systems are being used for visualization of deep tissue. Among such bioluminescence systems, the luminescence system of fireflies is known to have excellent luminescence efficiency. In the luminescence system of fireflies, firefly luciferin ($LH_2$) serving as a luminescent substrate is converted to oxyluciferin in an excited state with firefly luciferase (Luc) serving as a luminescence enzyme in the presence of adenosine triphosphate (ATP) and magnesium ions ($Mg^{2+}$), and then yellow-green light having a wavelength of approximately 560 nm is emitted when this oxyluciferin relaxes to a ground state.

Recently, compounds enabling a variety of luminescence wavelengths have been synthesized as luminescent substrate analogues for the luminescence system of fireflies. For example, Patent Literature (PTL) 1 to 3, listed below, disclose luminescent substrates having a molecular structure analogous to that of firefly luciferin. Among such firefly luciferin analogues, luminescent substrates that emit light of a long wavelength are promising as marking materials for visualizing a focus of disease in deep tissue due to long wavelength light having high biopermeability. For example, a compound represented by the following structural formula (a), a compound represented by the following structural formula (b), and a compound represented by the following structural formula (c) are disclosed to each display a luminescence spectrum with a maximum wavelength of roughly 670 nm in PTL 1 to 3, respectively. These materials enable visualization at a microcellular level in deep tissue that has not been possible with optical imaging up until now.

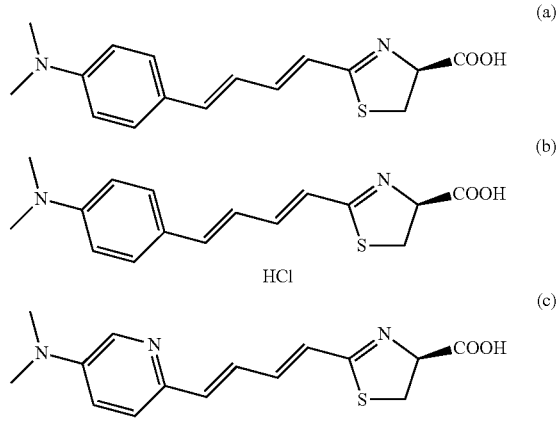

Moreover, Non-Patent Literature (NPL) 1, listed below, discloses a luminescence enzyme (AkaLuc) created through genetic modification from firefly luciferase (Luc), the natural luminescence enzyme of fireflies, as a luminescence enzyme specialized for a compound represented by structural formula (a) or (c). The use of this specialized enzyme can provide higher brightness, enables visualization of a single cancer cell inside mouse lung and of mouse brain in vivo, and also enables visualization of deep brain striatum in primate marmoset. Thus, optical imaging having high spatial resolution of a different level to that of X-rays or MRI and enabling accurate visualization marking from the single cell level is a fundamental tool in the life sciences.

CITATION LIST

Patent Literature

PTL 1: JP2009-184932A
PTL 2: JP2014-218456A
PTL 3: JP2015-193584A

Non-Patent Literature

NPL 1: Science, 359, 935-939 (2018)

SUMMARY

Technical Problem

However, there are only a small number of compounds such as those represented by structural formulae (a), (b), and (c) that have been put into practice as materials enabling near infrared luminescence marking, and even the compounds represented by structural formulae (a), (b), and (c) generally have low luminescence intensity and cannot emit light with high brightness unless used in combination with the specialized enzyme described above.

Accordingly, an object of the present disclosure is to solve the problem in the conventional techniques described above and provide a novel compound that can emit light with high brightness and can be used as a luminescent substrate in a firefly bioluminescence system.

Solution to Problem

As a result of diligent studies aimed at solving the problem set forth above, the inventors discovered that a compound having a specific structure, or a salt thereof, functions as a luminescent substrate in a firefly bioluminescence system and also emits light with high brightness, and, in this manner, the inventors completed the present disclosure.

Specifically, the present disclosure provides a heterocyclic compound represented by the following general formula (1):

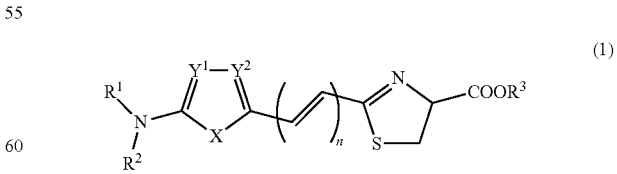

where $R^1$, $R^2$, and $R^3$ are each independently hydrogen or an alkyl group having a carbon number of 1 to 4, with provisos that $R^1$ and $R^2$ are optionally bonded to each other to form a ring and that one of $R^1$ and $R^2$ is optionally bonded to $Y^1$ to form a ring, X is S, O, NR⁴, or CH₂, and $Y^1$ and $Y^2$ are each independently N or $CR^4$, where each $R^4$ is independently hydrogen, an alkyl group having a carbon number of 1 to 4, an alkenyl group having a carbon number of 2 to 4, or an acyl group having a carbon number of 2 to 4, and n is an integer of 0 to 4.

This heterocyclic compound according to the present disclosure functions as a luminescent substrate in a firefly bioluminescence system and can emit light with high brightness.

In a preferred example of the heterocyclic compound according to the present disclosure, either or both of $Y^1$ and $Y^2$ are N. In this case, luminescence efficiency improves.

In another preferred example of the heterocyclic compound according to the present disclosure, X is S. Luminescence efficiency also improves in this case.

The heterocyclic compound according to the present disclosure is particularly preferably a compound represented by the following structural formula (1-1) or (1-2).

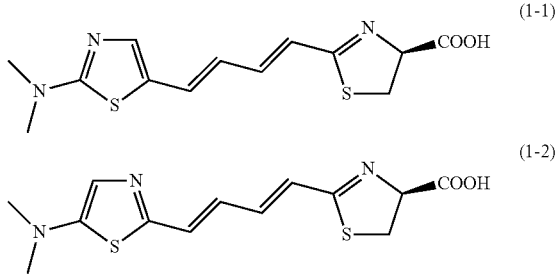

A compound represented by structural formula (1-1) or (1-2) can emit light with even higher brightness and can emit light having a long wavelength, and thus is useful for visualization of deep tissue.

The present disclosure also provides a salt of the heterocyclic compound set forth above, and this salt also functions as a luminescent substrate in a firefly bioluminescence system and can emit light with high brightness.

The present disclosure also provides a luminescent substrate composition comprising the heterocyclic compound or salt thereof set forth above, and this luminescent substrate composition can form a firefly bioluminescence system together with a luminescence enzyme and can emit light with high brightness.

Advantageous Effect

According to the present disclosure, it is possible to provide a heterocyclic compound and salt thereof that can emit light with high brightness and can be used as a luminescent substrate in a firefly bioluminescence system.

DETAILED DESCRIPTION

Figure 1:
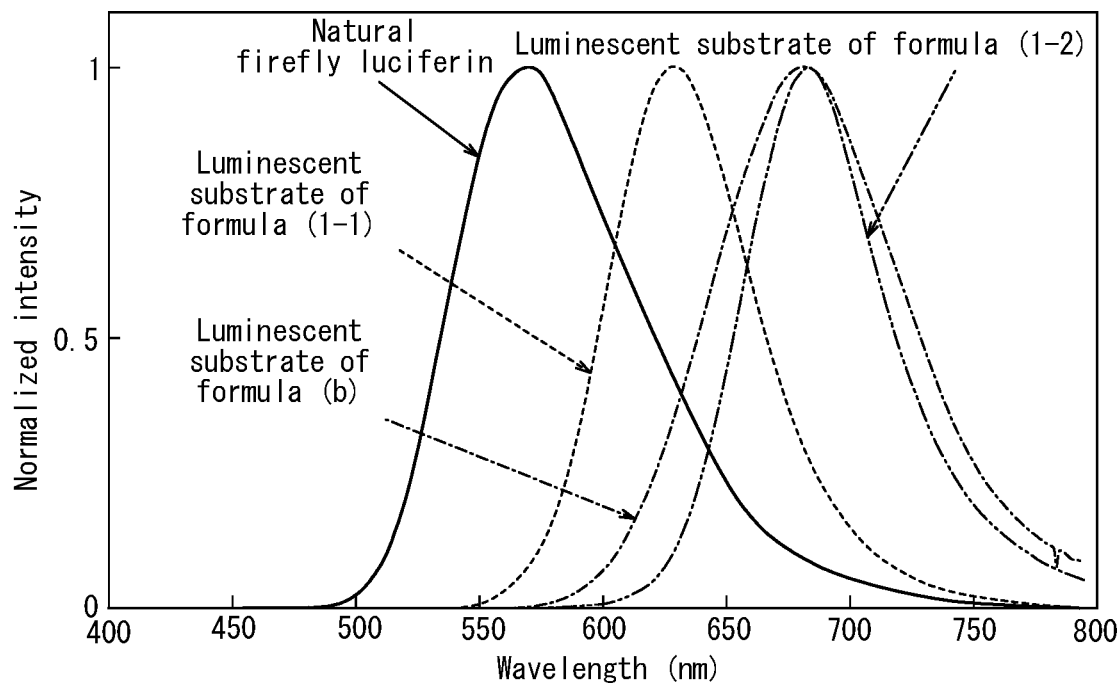
FIG. 1 is a luminescence spectrum normalized to give a maximum value for luminescence intensity of 1 for luminescence systems in which a compound represented by structural formula (1-1), a compound represented by structural formula (1-2), a compound represented by structural formula (b), and natural firefly luciferin are respectively used as luminescent substrates.

The following provides a detailed illustrative description of a heterocyclic compound, salt thereof, and luminescent substrate composition according to the present disclosure based on embodiments thereof.

<Heterocyclic Compound and Salt Thereof>

A feature of the heterocyclic compound according to the present disclosure is that it is represented by the following general formula (1).

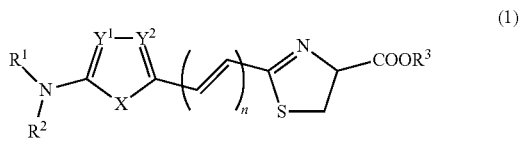

The heterocyclic compound according to the present disclosure includes another 5-membered heterocycle in addition to a dihydrothiazole ring and has a molecular structure analogous to firefly luciferin, and thus functions as a luminescent substrate in a firefly bioluminescence system. Moreover, the heterocyclic compound according to the present disclosure bonds more easily to firefly luciferase (Luc) serving as a luminescence enzyme and has higher luminescence efficiency than a compound represented by structural formula (a), (b), or (c) described above, and thus can emit light with high brightness.

The heterocyclic compound represented by general formula (1) may be in the form of a salt, and this salt also functions as a luminescent substrate in a firefly bioluminescence system and can emit light with high brightness.

In general formula (1), $R^1$, $R^2$, and $R^3$ are each independently hydrogen or an alkyl group having a carbon number of 1 to 4, with provisos that $R^1$ and $R^2$ are optionally bonded to each other to form a ring and that one of $R^1$ and $R^2$ is optionally bonded to $Y^1$ to form a ring.

The alkyl group having a carbon number of 1 to 4 may be a methyl group, an ethyl group, an n-propyl group, an isopropyl group, an n-butyl group, an isobutyl group, a sec-butyl group, a tert-butyl group, or the like. From a viewpoint of luminescence efficiency, $R^1$ and $R^2$ are preferably methyl groups. Likewise, from a viewpoint of luminescence efficiency, $R^3$ is preferably hydrogen.

A ring that $R^1$ and $R^2$ form with N when bonded to each other is preferably a 3- to 7-membered ring. A group that $R^1$ and $R^2$ form with N when bonded to each other is preferably a 1-azacyclopropyl group (3-membered ring), a 1-azacyclobutyl group (4-membered ring), a 1-azacyclopentyl group (5-membered ring), a 1-azacyclohexyl group (6-membered ring), a 1-azacycloheptyl group (7-membered ring), or the like, which are represented by the following formulae.

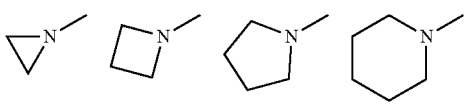

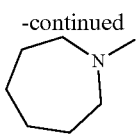

A ring formed by one of $R^1$ and $R^2$ bonding to $Y^1$ is preferably a 5-membered ring or a 6-membered ring. In this case, $Y^1$ is $CR^4$, and one of $R^1$ and $R^2$ is bonded to $R^4$ to form a ring structure.

In general formula (1), X is S, O, $NR^4$, or $CH_2$, and $Y^1$ and $Y^2$ are each independently N or $CR^4$.

From a viewpoint of luminescence efficiency, either or both of $Y^1$ and $Y^2$ are preferably N. Likewise, from a viewpoint of luminescence efficiency, X is preferably S.

With regards to X, $Y^1$, and $Y^2$ in general formula (1), each $R^4$ is independently hydrogen, an alkyl group having a carbon number of 1 to 4, an alkenyl group having a carbon number of 2 to 4, or an acyl group having a carbon number of 2 to 4. In a case in which either or both of $Y^1$ and $Y^2$ are $CR^4$, $R^4$ is preferably hydrogen.

The alkyl group having a carbon number of 1 to 4 may be a methyl group, an ethyl group, an n-propyl group, an isopropyl group, an n-butyl group, an isobutyl group, a sec-butyl group, a tert-butyl group, or the like.

The alkenyl group having a carbon number of 2 to 4 may be a vinyl group ($CH_2$=CH—), an allyl group ($CH_2$=$CHCH_2$—), a 1-propenyl group ($CH_3CH$=CH—), an isopropenyl group ($CH_2$=$C(CH_3)$—), a 1-butenyl group ($CH_3CH_2CH$=CH—), a 2-butenyl group ($CH_3CH$=$CHCH_2$—), a 3-butenyl group ($CH_2$=$CHCH_2CH_2$—), or the like.

The acyl group having a carbon number of 2 to 4 may be an acetyl group ($CH_3$—CO—), a propionyl group ($CH_3CH_2$—CO—), a butyryl group ($CH_3CH_2CH_2$—CO—), an isobutyryl group (($CH_3$)$_2$CH—CO—), an acryloyl group ($CH_2$=CH—CO—), a methacryloyl group ($CH_2$=C($CH_3$)—CO—), or the like.

In general formula (1), n is an integer of 0 to 4 that indicates the number of repetitions of a vinylene unit (—CH=CH—). A larger number for n results in a longer luminescence wavelength.

The optimal wavelength for bioimaging (i.e., the wavelength suitable for biopermeability) is 600 nm to 900 nm, which has a low tendency to be influenced by scattering and absorption by hemoglobin, oxyhemoglobin, and water. Therefore, n is preferably 2, 3, or 4 from a viewpoint of visualization of deep tissue and is preferably 2 or 3 from a viewpoint of ease of synthesis.

The heterocyclic compound represented by general formula (1) is preferably a compound represented by the following structural formula (1-1) or (1-2), and is particularly preferably a compound represented by structural formula (1-2).

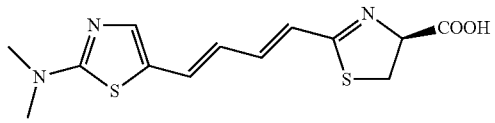

(1-1)

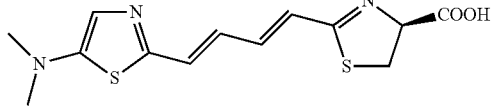

(1-2)

A heterocyclic compound that is represented by structural formula (1-1) or (1-2) and a salt thereof function as a luminescent substrate in a firefly bioluminescence system, can emit light with even higher brightness, and can emit light having a long wavelength, and thus are particularly useful for visualization of deep tissue. Moreover, a compound represented by structural formula (1-2) and a salt thereof are extremely useful for visualization of deep tissue because they can emit light having a long wavelength.

The heterocyclic compound represented by general formula (1) can be synthesized as described below, but is not specifically limited to being synthesized in this manner.

For example, an amine group-containing heterocyclic compound such as thiazol-2-amine, thiazol-5-amine, or triazol-2-amine may be adopted as a starting material and may be reacted with iodomethane as desired in order to obtain a dimethylamino product. Alternatively, a halogen (bromo group, etc.) containing heterocyclic compound such as 5-bromothiazole may be adopted as a starting material, and may be reacted with dimethylamine as desired in order to obtain a dimethylamino product. The dimethylamino product is then reacted with an alkyllithium such as normal butyllithium and is subsequently reacted with N,N-dimethylformamide (DMF) or the like to obtain an aldehyde product. Next, triethyl 4-phosphonocrotonate or the like is reacted with this aldehyde product in order to obtain an ester product while increasing the olefin number as desired. Next, the ester product is hydrolyzed to obtain a carboxyl product. This carboxyl product is then amidated using S-trityl-D-cysteine methyl ester (D-Cys(OMe)-STrt), 1-(3-dimethylaminopropyl)-3-ethylcarboimide hydrochloride (EDC), and N,N-dimethylaminopyridine (DMAP) in order to obtain an amide product. Next, this amide product is subjected to thiazoline cyclization using trifluoromethanesulfonic anhydride ($Tf_2O$) in order to obtain a thiazoline methyl ester product. The methyl ester moiety of the thiazoline methyl ester product is then hydrolyzed as desired in order to obtain a thiazoline ring-containing carboxyl product. Moreover, a desired heterocyclic compound can be obtained through appropriate alteration of the starting material, introduction of various substituents, or the like, or by adopting a different synthetic pathway.

The heterocyclic compound represented by general formula (1) may be in the form of a salt. In other words, the salt of the heterocyclic compound according to the present disclosure is a salt of the heterocyclic compound represented by general formula (1). This salt of the heterocyclic compound according to the present disclosure also functions as a luminescent substrate in a firefly bioluminescence system and can emit light with high brightness.

The salt of the heterocyclic compound according to the present disclosure may be an addition salt with an acid or may be an addition salt with a base. For example, in an addition salt of the heterocyclic compound according to the present disclosure and an acid, the acid may be hydrochloric acid, hydrobromic acid, hydroiodic acid, sulfuric acid, sulfamic acid, phosphoric acid, nitric acid, phosphorous acid, nitrous acid, citric acid, formic acid, acetic acid, oxalic acid, maleic acid, lactic acid, tartaric acid, fumaric acid, benzoic acid, mandelic acid, cinnamic acid, pamoic acid, stearic acid, glutamic acid, aspartic acid, methanesulfonic acid, ethanedisulfonic acid, p-toluenesulfonic acid, salicylic acid, succinic acid, trifluoroacetic acid, or the like, and the acid addition salt may be a hydrochloride, a hydrobromide, a hydroiodide, a sulfate, a sulfamate, a phosphate, a nitrate, a phosphite, a nitrite, a citrate, a formate, an acetate, an oxalate, a maleate, a lactate, a tartrate, a fumarate, a benzoate, a mandelate, a cinnamate, a pamoate, a stearate, a glutamate, an aspartate, a methanesulfonate, an ethanedisulfonate, a p-toluenesulfonate, a salicylate, a succinate, a trifluoroacetate, or the like. On the other hand, in an addition salt of the heterocyclic compound according to the present disclosure and a base, the base may be sodium hydroxide, potassium hydroxide, calcium hydroxide, or the like, and the base addition salt may be a sodium salt, a potassium salt, a calcium salt, or the like.

A salt of the heterocyclic compound represented by general formula (1) has excellent solubility in water or a buffer solution having a roughly neutral pH. Therefore, a salt of the heterocyclic compound represented by general formula (1) can be dissolved in high concentration in water or a buffer solution having a roughly neutral pH and can further improve luminescence brightness.

<Luminescent Substrate Composition>

The luminescent substrate composition according to the present disclosure contains the heterocyclic compound represented by general formula (1) described above or a salt thereof and may be composed of just the heterocyclic compound represented by general formula (1) or a salt thereof. The luminescent substrate composition according to the present disclosure can form a firefly bioluminescence system together with a luminescence enzyme such as natural firefly luciferase (Luc) or a mutant enzyme thereof and can emit light with high brightness.

By adding the above-described heterocyclic compound or salt thereof according to the present disclosure into a system in which luminescent beetle luciferase, adenosine triphosphate (ATP), and magnesium ions ($Mg^{2+}$) are present, the compound or salt is oxidized through the luminescent beetle luciferase and emits light. Note that the heterocyclic compound or salt thereof according to the present disclosure may be provided as a luminescent detection kit (luminescent substrate composition) together with ATP and $Mg^{2+}$, and this luminescent detection kit may contain another luminescent substrate or a solution adjusted to an appropriate pH.

In a situation in which the heterocyclic compound or salt thereof according to the present disclosure is adopted in a luminescence system, the heterocyclic compound or salt thereof according to the present disclosure is preferably used in a concentration of 1 µM or more, and more preferably in a concentration of 5 µM or more in order to obtain suitable luminescence intensity. In other words, the luminescent substrate composition according to the present disclosure preferably contains the above-described heterocyclic compound represented by general formula (1) or a salt thereof in a concentration of 1 µM or more, and more preferably in a concentration of 5 µM or more. The pH of the luminescent substrate composition according to the present disclosure and the pH of the luminescence system are preferably 4 to 10, and more preferably 6 to 8. A buffering agent such as potassium phosphate, tris hydrochloride, glycerin, or HEPES may be included for pH stabilization as necessary. Moreover, in a case in which the luminescent substrate composition (luminescent detection kit) contains ATP, the concentration of ATP is preferably 4 µM or more, and more preferably 20 µM or more.

The heterocyclic compound or salt thereof according to the present disclosure can be caused to emit light through various luminescence enzymes (oxidizing enzymes) in a firefly luminescent beetle luciferase luminescence system. The luciferase may be isolated from a North American firefly (*Photinus pyralis*), a railroad worm, or the like, and any of these can be used. Further examples of oxidizing enzymes that can be used include pyrophorus click beetle luciferase, Iriomote firefly luciferase, and flavin-containing monooxygenase. Moreover, a mutant enzyme of natural firefly luciferase can also be used as a luminescence enzyme.

In bioluminescence using the heterocyclic compound or salt thereof according to the present disclosure as a luminescent substrate, luminescence is enhanced by the presence of coenzyme A (CoA), pyrophosphoric acid, or magnesium ions ($Mg^{2+}$) in the luminescence system. The luminescence enhancement effect of these compounds is evident when the concentration of CoA, pyrophosphoric acid, or $Mg^{2+}$ in the luminescence system is 5 µM or more, and luminescence is enhanced with increasing concentration.

In order to use a firefly bioluminescence system for measurement/detection, it is preferable to stabilize luminescence (for example, to preferably provide magnesium ions in the luminescence system, and more preferably provide both magnesium ions and pyrophosphoric acid in the luminescence system) such that enzyme deactivation is prevented and plateau like luminescence behavior is displayed. Note that in a case in which only magnesium ions are used, the concentration of magnesium ions in the luminescence system is preferably 0.5 mM or more from a viewpoint of stabilization of luminescence, and stability of luminescence improves with increasing concentration. Moreover, in a case in which magnesium pyrophosphate is used, the concentration of magnesium pyrophosphate in the luminescence system is preferably 10 µM or more, and more preferably 100 µM or more from a viewpoint of stabilization of luminescence. Note that the ratio of pyrophosphoric acid and magnesium ions does not necessarily need to be an equivalent ratio. Examples of suitable magnesium salts include inorganic acid salts such as magnesium sulfate and magnesium chloride, and organic acid salts such as magnesium acetate. Examples of suitable pyrophosphate salts include pyrophosphates of alkali metals such as sodium and potassium, pyrophosphates of alkaline earth metals such as magnesium and calcium, and pyrophosphates of iron.

The heterocyclic compound or salt thereof according to the present disclosure can be used for luminescent marking in biological measurement/detection and can, for example, be used for marking of amino acid, polypeptide, protein, nucleic acid, or the like. It should be noted that methods by which the heterocyclic compound or salt thereof according to the present disclosure can be caused to bond to these substances are common knowledge for a person skilled in the art. For example, the heterocyclic compound or salt thereof according to the present disclosure can be caused to bond to a carboxyl group or amino group of a target substance using a method that is commonly known by a person skilled in the art.

Moreover, the heterocyclic compound or salt thereof according to the present disclosure can be used in measurement/detection using detection of activity of luminescent beetle luciferase through luminescence of a luminescent substrate. For example, by administering the heterocyclic compound or salt thereof according to the present disclosure to a cell or animal into which a luciferase gene has been introduced, it is possible to measure/detect expression of the target gene or protein in vivo. Note that light of a long wavelength has high optical transmittivity and also has high tissue permeability. Therefore, among heterocyclic compounds and salts thereof that are in accordance with the present disclosure, those that luminesce with a long wavelength are useful as marking materials for visualization of deep tissue.

EXAMPLES

The following provides a more detailed description of the present disclosure through examples. However, the present disclosure is not in any way limited to the following examples.

<Synthesis of Compound Represented by Structural Formula (1-1)>

Synthesis of N,N-dimethylthiazol-2-amine (3)

Thiazol-2-amine (2) (1.00 g, 10.0 mmol) was dissolved in THF (30 mL), and then iodomethane (2.0 mL, 32 mmol) was added and stirred therewith. This mixed solution was cooled to 0° C., and NaH (60% in oil, 1.61 g, 40.2 mmol) was gradually added and stirred therewith for 50 minutes. In an ice bath, the reaction was quenched through addition of methanol, extraction was performed with chloroform (100 mL×3), and washing was performed with saturated saline, and then concentrating was performed under reduced pressure. The resultant residue was subsequently purified by silica column chromatography (hexane/ethyl acetate=1/1) to yield N,N-dimethylthiazol-2-amine (3) (853 mg, 6.66 mol, 67%) as a brown oil.

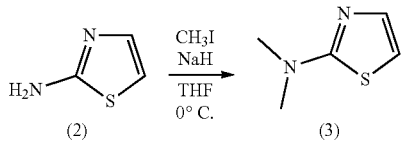

Results of identification of N,N-dimethylthiazol-2-amine (3)

$^1$H NMR (400 MHz, CDCl$_3$) δ 7.19 (d, J=3.7 Hz, 1H), 6.50 (d, J=3.7 Hz, 1H), 3.11 (s, 6H)

$^{13}$C NMR (101 MHz, CDCl$_3$) δ 171.9, 139.8, 106.6, 40.3

HR-MS: m/z: [M+H]$^+$ calculated for C$_5$H$_9$N$_2$S: 129.0486; measured: 129.0491

Synthesis of 2-(dimethylamino)thiazole-5-carbaldehyde (4)

N,N-Dimethylthiazol-2-amine (3) (763 mg, 5.95 mmol) was dissolved in anhydrous THF (15 mL), was cooled to −80° C., and was stirred under an Ar atmosphere. A hexane solution of n-BuLi (1.6 M, 5.6 mL, 9.0 mmol) was gradually added dropwise to this mixed solution and was stirred therewith for 60 minutes. Thereafter, anhydrous DMF (1.5 mL) was added, the temperature was raised to room temperature, and a further 90 minutes of stirring was performed. Once exhaustion of raw material was confirmed, the reaction was quenched through addition of water in an ice bath, extraction was performed with chloroform (50 mL×3), washing was performed with saturated saline, and then concentrating was performed under reduced pressure. The resultant residue was subsequently purified by silica column chromatography (hexane/ethyl acetate=1/1) to quantitatively yield 2-(dimethylamino)thiazole-5-carbaldehyde (4) (931 mg, 5.96 mmol) as a yellow solid.

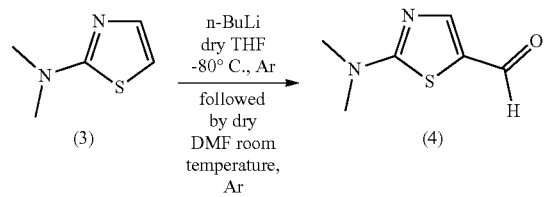

Results of identification of 2-(dimethylamino)thiazole-5-carbaldehyde (4)

$^1$H NMR (400 MHz, CDCl$_3$) δ 9.68 (s, 1H), 7.88 (s, 1H), 3.23 (s, 6H)

$^{13}$C NMR (101 MHz, CDCl$_3$) δ 180.7, 176.1, 153.9, 129.0, 40.6

HR-MS: m/z: [M+Na]$^+$ calculated for C$_6$H$_8$N$_2$ONa: 179.0255; measured: 179.0261

Synthesis of ethyl (2E,4E)-5-(2-(dimethylamino)thiazol-5-yl)penta-2,4-dienoate (5)

2-(Dimethylamino)thiazole-5-carbaldehyde (4) (452 mg, 2.89 mmol) was dissolved in THF (10 mL), and then triethyl 4-phosphonocrotonate (730 μL, 3.29 mmol) was added and stirred therewith at 0° C. NaH (60% in oil, 237 mg, 5.91 mmol) was gradually added to this mixed solution and was stirred therewith for 3 hours. In an ice bath, the reaction was quenched through addition of ethanol, extraction was performed with ethyl acetate (80 mL×3), and washing was performed with saturated saline, and then concentrating was performed under reduced pressure. The resultant residue was subsequently purified by silica column chromatography (hexane/ethyl acetate=1/1) to yield ethyl (2E,4E)-5-(2-(dimethylamino)thiazol-5-yl)penta-2,4-dienoate (5) (405 mg, 1.61 mmol, 55%) as yellow crystals.

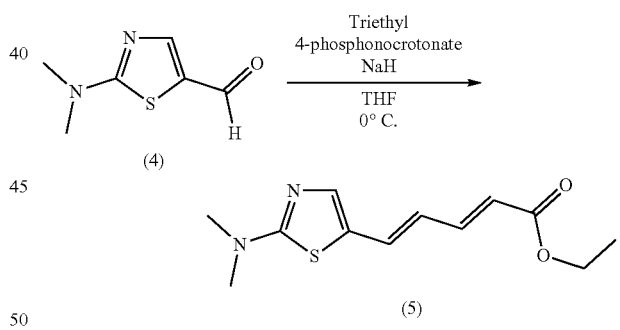

Results of identification of ethyl (2E,4E)-5-(2-(dimethylamino)thiazol-5-yl)penta-2,4-dienoate (5)

$^1$H NMR (400 MHz, CDCl$_3$) δ 7.35 (dd, J=15.2, 11.2 Hz, 1H), 7.22 (s, 1H), 6.88 (d, J=15.2 Hz, 1H), 6.23 (dd, J=15.2, 11.2 Hz, 1H), 5.82 (d, J=15.2 Hz, 1H), 4.21 (q, J=7.2 Hz, 2H), 3.15 (s, 6H), 1.30 (t, J=7.2 Hz, 3H)

$^{13}$C NMR (101 MHz, CDCl$_3$) δ 171.2, 167.5, 144.9, 143.5, 131.3, 125.7, 123.2, 118.7, 60.3, 40.4, 14.5

HR-MS: m/z: [M+H]$^+$ calculated for C$_{12}$H$_{17}$N$_2$O$_2$S: 253.1011; measured: 253.1012

Synthesis of (2E,4E)-5-(2-(dimethylamino)thiazol-5-yl)penta-2,4-dienoic acid (6)

Ethyl (2E,4E)-5-(2-(dimethylamino)thiazol-5-yl)penta-2,4-dienoate (5) (323 mg, 1.28 mmol) was dissolved in i-PrOH (10 mL), and then NaOH aqueous solution (1 M, 1 mL) was added and stirred therewith while being heated under reflux. Once exhaustion of raw material was confirmed, the temperature of the mixed solution was lowered to room temperature. Neutralization with HCl aqueous solution was then performed under stirring in an ice bath, and then concentrating was performed under reduced pressure. The resultant residue was subsequently purified by silica column chromatography (chloroform/methanol=5/1) to yield (2E,4E)-5-(2-(dimethylamino)thiazol-5-yl)penta-2,4-dienoic acid (6) (282 mg, 1.26 mmol, 98%) as yellow crystals.

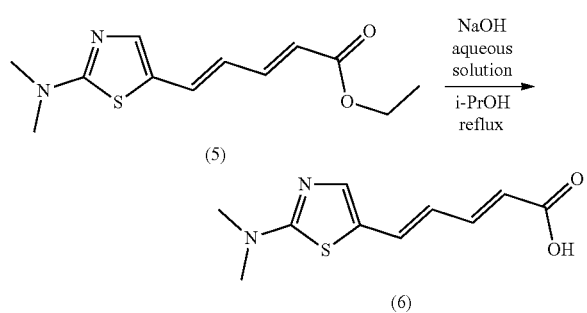

Results of identification of (2E,4E)-5-(2-(dimethylamino)thiazol-5-yl)penta-2,4-dienoic acid (6)

$^1$H NMR (400 MHz, DMSO-$d_6$) δ 7.32 (s, 1H), 7.23 (dd, J=15.2, 11.2 Hz, 1H), 7.09 (d, J=15.2 Hz, 1H), 6.30 (dd, J=15.2, 11.2 Hz, 1H), 5.83 (d, J=15.2 Hz, 1H), 3.09 (s, 6H)

$^{13}$C NMR (101 MHz, DMSO-$d_6$) δ 170.4, 167.9, 144.5, 144.0, 131.2, 124.9, 122.7, 119.4, 39.8

HR-MS: m/z: [M+H]$^+$ calculated for $C_{10}H_{13}N_2O_2S$: 225.0698; measured: 225.0702

Synthesis of N-((2E,4E)-5-(2-(dimethylamino)thiazol-5-yl)penta-2,4-dienoyl)-S-trityl-D-cysteine methyl ester (7)

(2E,4E)-5-(2-(Dimethylamino)thiazol-5-yl)penta-2,4-dienoic acid (6) (113 mg, 504 μmol) was dissolved in DMF (8 mL), and then EDC (194.3 mg, 1.01 mmol), DMAP (77.3 mg, 633 μmol), and D-Cys(OMe)-STrt HCl (258.1 mg, 623 μmol) were added and stirred therewith at room temperature under an Ar atmosphere. Once exhaustion of raw material was confirmed, water was added under stirring in an ice bath, and then extraction was performed with ethyl acetate (50 mL×3), and concentrating was performed under reduced pressure. The resultant residue was subsequently purified by silica column chromatography (hexane/ethyl acetate=1/2) to yield N-((2E,4E)-5-(2-(dimethylamino)thiazol-5-yl)penta-2,4-dienoyl)-S-trityl-D-cysteine methyl ester (7) (273 mg, 468 μmol, 93%) as yellow crystals.

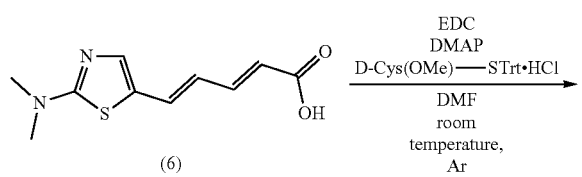

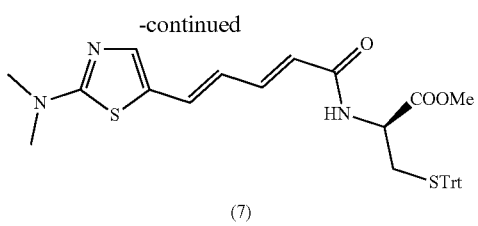

Results of identification of N-((2E,4E)-5-(2-(dimethylamino)thiazol-5-yl)penta-2,4-dienoyl)-S-trityl-D-cysteine methyl ester (7)

$^1$H NMR (400 MHz, CDCl$_3$) δ 7.39-7.36 (m, 6H), 7.30-7.20 (m, 10H), 6.86 (d, J=14.9 Hz, 1H), 6.22 (dd, J=14.9, 11.2 Hz, 1H), 5.95-5.91 (m, 1H), 5.77 (d, J=14.9 Hz, 1H), 4.75-4.71 (m, 1H), 3.72 (s, 3H), 3.15 (s, 6H), 2.73-2.65 (m, 2H)

$^{13}$C NMR (101 MHz, CDCl$_3$) δ 171.1, 171.0, 165.7, 144.3, 143.0, 142.0, 130.6, 129.5, 128.0, 126.9, 125.7, 123.1, 120.5, 66.9, 52.7, 51.1, 40.2, 34.1

HR-MS: m/z: [M+H]$^+$ calculated for $C_{33}H_{34}N_3O_3S_2$: 584.2042; measured: 584.2044

Synthesis of (S)-2-((1E,3E)-4-(2-(dimethylamino)thiazol-5-yl)buta-1,3-dien-1-yl)-4,5-dihydrothiazole-4-carboxylic acid methyl ester (8)

Tf$_2$O (60 μL, 366 μmol) was added to CH$_2$Cl$_2$ (0.5 mL) and stirred therewith in an ice bath under an Ar atmosphere. N-((2E,4E)-5-(2-(Dimethylamino)thiazol-5-yl)penta-2,4-dienoyl)-S-trityl-D-cysteine methyl ester (7) (101 mg, 173 μmol) dissolved in CH$_2$Cl$_2$ (2.5 mL) was slowly added dropwise and was stirred therewith for 45 minutes. Once exhaustion of raw material was confirmed, saturated sodium bicarbonate water was added under stirring in an ice bath to perform neutralization, extraction was then performed with chloroform (50 mL×3), and concentrating was performed under reduced pressure. The resultant residue was subsequently purified by silica column chromatography (hexane/ethyl acetate=1/3) to yield (S)-2-((1E,3E)-4-(2-(dimethylamino)thiazol-5-yl)buta-1,3-dien-1-yl)-4,5-dihydrothiazole-4-carboxylic acid methyl ester (8) (47.5 mg, 147 μmol, 85%) as a brown-yellow solid.

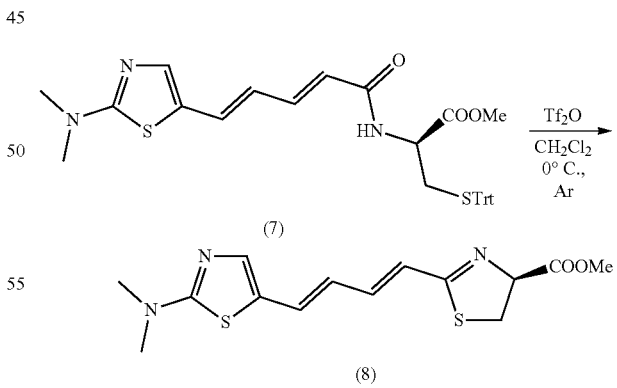

Results of identification of (S)-2-((1E,3E)-4-(2-(dimethylamino)thiazol-5-yl)buta-1,3-dien-1-yl)-4,5-dihydrothiazole-4-carboxylic acid methyl ester (8)

$^1$H NMR (400 MHz, CDCl$_3$) δ 7.20 (s, 1H), 6.88-6.80 (m, 2H), 6.48 (d, J=15.4 Hz, 1H), 6.24 (dd, J=14.8, 10.9 Hz, 1H), 5.16 (t, J=9.0 Hz, 1H), 3.83 (s, 3H), 3.61-3.50 (m, 2H), 3.15 (s, 6H)

$^{13}$C NMR (101 MHz, CDCl$_3$) δ 171.5, 171.1, 170.1, 143.1, 142.8, 129.7, 125.8, 123.9, 123.0, 77.9, 52.9, 40.3, 34.7

HR-MS: m/z: [M+H]$^+$ calculated for C$_{14}$H$_{18}$N$_3$O$_2$S$_2$: 324.0840; measured: 324.0838

Synthesis of (S)-2-((1E,3E)-4-(2-(dimethylamino)thiazol-5-yl)buta-1,3-dien-1-yl)-4,5-dihydrothiazole-4-carboxylic acid (1-1)

(S)-2-((1E,3E)-4-(2-(Dimethylamino)thiazol-5-yl)buta-1,3-dien-1-yl)-4,5-dihydrothiazole-4-carboxylic acid methyl ester (8) (23.6 mg, 73 μmol) was suspended in ultrapure water (1 mL), 6 M HCl (1 mL) was added thereto, and this solution was stirred at room temperature for 18 hours. The reaction mixture was neutralized through addition of sodium bicarbonate and was subsequently concentrated under reduced pressure. The resultant residue was purified by automated flash column chromatography (Smart Flash EPCLC AI-580S, ULTRAPACK COLUMNS C$_{18}$, H$_2$O/methanol=9/1→1/9) to quantitatively yield (S)-2-((1E,3E)-4-(2-(dimethylamino)thiazol-5-yl)buta-1,3-dien-1-yl)-4,5-dihydrothiazole-4-carboxylic acid (1-1) (29.5 mg, 95 μmol).

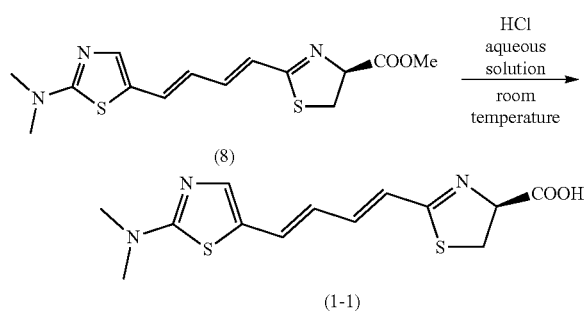

Results of identification of (S)-2-((1E,3E)-4-(2-(dimethylamino)thiazol-5-yl)buta-1,3-dien-1-yl)-4,5-dihydrothiazole-4-carboxylic acid (1-1)

$^1$H NMR (500 MHz, CD$_3$OD) δ 7.19 (s, 1H), 6.93-6.85 (m, 2H), 6.47 (d, J=14.9 Hz, 1H), 6.34 (dd, J=15.2, 10.6 Hz, 1H), 4.98-4.92 (m, 1H), 3.55-3.45 (m, 2H), 3.13 (s, 6H)

HR-MS: m/z: [M+H]$^+$ calculated for C$_{13}$H$_{16}$N$_3$O$_2$S$_2$: 310.0684; measured: 310.0682

<Synthesis of Compound Represented by Structural Formula (1-2)>

Synthesis of N,N-dimethylthiazol-5-amine (10)

5-Bromothiazole (9) (1.72 g, 10.5 mmol) was dissolved in 1,2-dimethoxyethane (DME) (30 mL) and DMF (20 mL), and then NHMe$_2$ (50% in water, 3.5 mL, 32 mmol) was added and stirred therewith. tBuONa (2.03 g, 21.1 mmol), Rh(cod)$_2$BF$_4$ (87.5 mg, 215 μmol), and 1,3-diisopropylimidazolium chloride (81.5 mg, 432 μmol) were added and were stirred therewith at 80° C. under an Ar atmosphere for 16 hours. Once exhaustion of raw material was confirmed, the temperature was lowered to room temperature, and suction filtration was performed using silica. The filtrate was washed with water and saline, and then the organic layer was concentrated to yield N,N-dimethylthiazol-5-amine (10) (1.08 g, 8.40 mmol, 80%) as a brown oil.

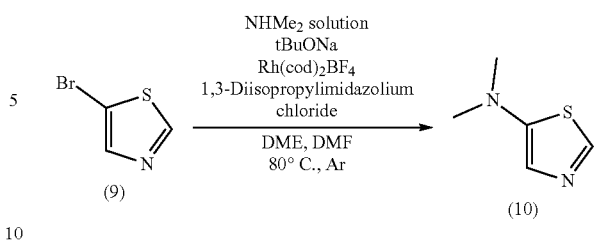

Results of identification of N,N-dimethylthiazol-5-amine (10)

$^1$H NMR (400 MHz, CDCl$_3$) δ 8.08 (s, 1H), 6.85 (s, 1H), 2.92 (s, 6H)

$^{13}$C NMR (101 MHz, CDCl$_3$) δ 155.3, 139.0, 120.4, 43.8×2

HR-MS: m/z: [M+H]$^+$ calculated for C$_5$H$_9$N$_2$S: 129.0486; measured: 129.0486

Synthesis of 5-(dimethylamino)thiazole-2-carbaldehyde (11)

N,N-Dimethylthiazol-5-amine (10) (1.80 g, 14.0 mmol) was dissolved in anhydrous THF (60 mL), was cooled to −80° C., and was stirred under an Ar atmosphere. A hexane solution of n-BuLi (1.6 M, 14.0 mL, 22.4 mmol) was gradually added dropwise to this mixed solution and was then stirred therewith for 90 minutes. Thereafter, anhydrous DMF (4 mL) was added, the temperature was raised to room temperature, and a further 2 hours of stirring was performed. Once exhaustion of raw material was confirmed, the reaction was quenched through addition of water in an ice bath, extraction was performed with ethyl acetate (150 mL×3), washing was performed with saturated saline, and then concentrating was performed under reduced pressure. The resultant residue was subsequently purified by silica column chromatography (hexane/ethyl acetate=1/1) to yield 5-(dimethylamino)thiazole-5-carbaldehyde (11) (875 mg, 5.60 mmol) as a yellow solid.

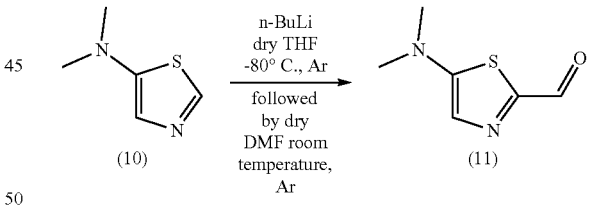

Results of identification of 5-(dimethylamino)thiazole-2-carbaldehyde (11)

$^1$H NMR (400 MHz, CDCl$_3$) δ 9.67 (s, 1H), 7.06 (s, 1H), 3.13 (s, 6H)

$^{13}$C NMR (101 MHz, CDCl$_3$) δ 182.1, 162.7, 148.6, 122.9, 42.9×2

HR-MS: m/z: [M+Na]$^+$ calculated for C$_6$H$_8$N$_2$ONaS: 179.0255; measured: 179.0251

Synthesis of ethyl (2E,4E)-5-(5-(dimethylamino)thiazol-2-yl)penta-2,4-dienoate (12)

5-(Dimethylamino)thiazol-2-carbaldehyde (11) (875 mg, 5.60 mmol) was dissolved in THF (50 mL), and then triethyl 4-phosphonocrotonate (90%) (1.67 mL, 6.72 mmol) was added and was stirred therewith in an ice bath. NaH (60% in oil, 293 mg, 7.34 mmol) was gradually added to this mixed solution and was stirred therewith for 15 minutes. In an ice bath, the reaction was quenched through addition of ethanol, extraction was performed with ethyl acetate (150 mL×3), and washing was performed with saturated saline, and then concentrating was performed under reduced pressure. The resultant residue was subsequently purified by silica column chromatography (hexane/ethyl acetate=1/1) to yield ethyl (2E,4E)-5-(5-(dimethylamino)thiazol-2-yl)penta-2,4-dienoate (12) (1.02 g, 4.03 mmol, 72%) as yellow crystals.

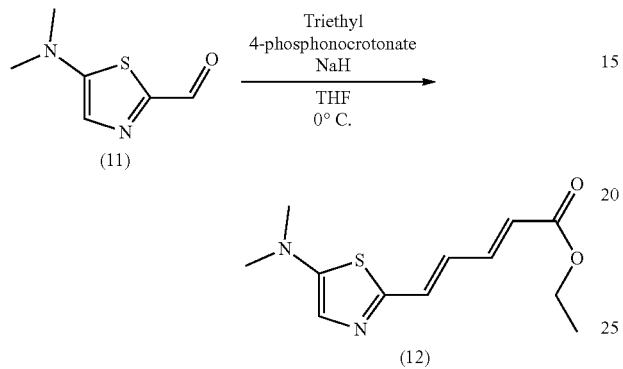

Results of identification of ethyl (2E,4E)-5-(5-(dimethylamino)thiazol-2-yl)penta-2,4-dienoate (12)

$^1$H NMR (400 MHz, CDCl$_3$) δ 7.38 (dd, J=15.2, 11.3 Hz, 1H), 6.91 (d, J=15.4 Hz, 1H), 6.76 (s, 1H), 6.70 (dd, J=15.4, 11.3 Hz, 1H), 5.95 (d, J=15.2 Hz, 1H), 4.22 (q, J=7.1 Hz, 2H), 3.00 (s, 6H), 1.31 (t, J=7.1 Hz, 3H)

$^{13}$C NMR (101 MHz, CDCl$_3$) δ 167.1, 156.7, 149.9, 143.8, 133.4, 126.3, 121.4, 120.9, 60.5, 43.4×2, 14.5

HR-MS: m/z: [M+H]$^+$ calculated for C$_{12}$H$_{17}$N$_2$O$_2$S: 253.1011; measured: 253.1003

Synthesis of (2E,4E)-5-(5-(dimethylamino)thiazol-2-yl)penta-2,4-dienoic acid (13)

Ethyl (2E,4E)-5-(5-(dimethylamino)thiazol-2-yl)penta-2,4-dienoate (12) (1.00 g, 3.96 mmol) was dissolved in i-PrOH (35 mL), and then NaOH aqueous solution (5 M, 1 mL) was added and was stirred therewith while being heated under reflux for 2.5 hours. Once exhaustion of raw material was confirmed, the temperature of the mixed solution was lowered to room temperature. The mixed solution was then neutralized with HCl aqueous solution while being stirred in an ice bath, and was concentrated under reduced pressure. The resultant residue was subsequently purified by silica column chromatography (chloroform/methanol=5/1) to quantitatively yield (2E,4E)-5-(5-(dimethylamino)thiazol-2-yl)penta-2,4-dienoic acid (13) (911 mg, 4.06 mmol, 103%) as yellow crystals.

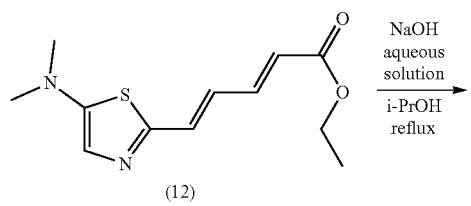

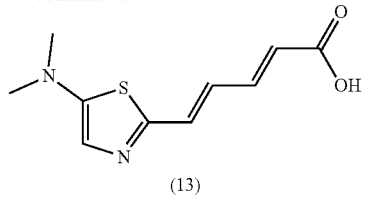

Results of identification of (2E,4E)-5-(5-(dimethylamino)thiazol-2-yl)penta-2,4-dienoic acid (13)

$^1$H NMR (400 MHz, DMSO-d$_6$) δ 7.32 (dd, J=15.2, 11.3 Hz 1H), 7.05 (d, J=15.4 Hz, 1H), 6.87 (s, 1H), 6.79 (dd, J=15.4, 11.3 Hz, 1H), 5.99 (d, J=15.2 Hz, 1H), 2.96 (s, 6H)

$^{13}$C NMR (101 MHz, DMSO-d$_6$) δ 167.5, 156.4, 148.2, 143.4, 132.8, 125.8, 121.9, 120.5, 42.7×2

HR-MS: m/z: [M−H]$^−$ calculated for C$_{10}$H$_{11}$N$_2$O$_2$S: 223.0541; measured: 223.0533

Synthesis of N-((2E,4E)-5-(5-(dimethylamino)thiazol-2-yl)penta-2,4-dienoyl)-S-trityl-D-cysteine methyl ester (14)

(2E,4E)-5-(5-(Dimethylamino)thiazol-2-yl)penta-2,4-dienoic acid (13) (904 mg, 4.03 mmol) was dissolved in DMF (46 mL), and then EDC (1.53 g, 7.99 mmol), DMAP (600 mg, 4.91 mmol), and D-Cys(OMe)-STrt HCl (2.01 g, 4.85 mmol) were added and were stirred therewith at room temperature under an Ar atmosphere for 16 hours. Once exhaustion of raw material was confirmed, water was added under stirring in an ice bath, extraction was performed with ethyl acetate (50 mL×3), and then concentrating was performed under reduced pressure. The resultant residue was subsequently purified by silica column chromatography (hexane/ethyl acetate=1/2) to yield N-((2E,4E)-5-(5-(dimethylamino)thiazol-2-yl)penta-2,4-dienoyl)-S-trityl-D-cysteine methyl ester (14) (1.73 g, 2.96 mmol, 73%) as yellow crystals.

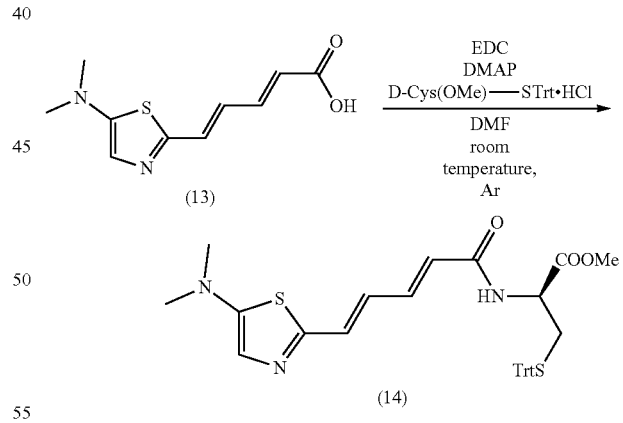

Results of identification of N-((2E,4E)-5-(5-(dimethylamino)thiazol-2-yl)penta-2,4-dienoyl)-S-trityl-D-cysteine methyl ester (14)

$^1$H NMR (400 MHz, CDCl$_3$) δ 7.39-7.20 (m, 16H), 6.86 (d, J=15.1 Hz, 1H), 6.76 (s, 1H), 6.70 (dd, J=15.4, 11.3 Hz, 1H), 5.98 (d, J=7.9 Hz, 1H, CONH), 5.89 (d, J=14.9 Hz, 1H), 4.75-4.70 (m, 1H), 3.72 (s, 3H), 2.99 (s, 6H), 2.75-2.66 (m, 2H)

$^{13}$C NMR (101 MHz, CDCl$_3$) δ 171.1, 165.4, 156.5, 150.2, 144.4×3, 141.2, 132.9, 129.6×6, 128.2×6, 127.1×3, 126.3, 123.2, 120.8, 67.1, 52.8, 51.3, 43.4×2, 34.1

HR-MS: m/z: [M+Na]$^+$ calculated for $C_{33}H_{33}N_3O_3NaS_2$: 606.1861; measured: 606.1862

Synthesis of (S)-2-((1E,3E)-4-(5-(dimethylamino)thiazol-2-yl)buta-1,3-dien-1-yl)-4,5-dihydrothiazole-4-carboxylic acid methyl ester (15)

Tf$_2$O (400 µL, 2.44 mmol) was added to CH$_2$Cl$_2$ (5 mL) and stirred therewith in an ice bath under an Ar atmosphere. N-((2E,4E)-5-(5-(Dimethylamino)thiazol-2-yl)penta-2,4-dienoyl)-S-trityl-D-cysteine methyl ester (14) (714 mg, 1.22 mmol) dissolved in CH$_2$Cl$_2$ (10 mL) was slowly added dropwise and was stirred therewith for 35 minutes. Once exhaustion of raw material was confirmed, saturated sodium bicarbonate water was added under stirring in an ice bath to perform neutralization, extraction was then performed with chloroform (100 mL×3), and concentrating was performed under reduced pressure. The resultant residue was subsequently purified by silica column chromatography (hexane/ethyl acetate=1/3) to yield (S)-2-((1E,3E)-4-(5-(dimethylamino)thiazol-2-yl)buta-1,3-dien-1-yl)-4,5-dihydrothiazole-4-carboxylic acid methyl ester (15) (102 mg, 316 µmol, 26%) as a brown-yellow solid.

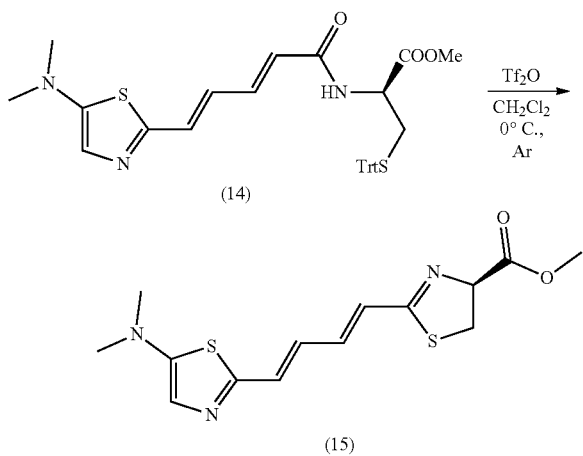

Results of identification of (S)-2-((1E,3E)-4-(5-(dimethylamino)thiazol-2-yl)buta-1,3-dien-1-yl)-4,5-dihydrothiazole-4-carboxylic acid methyl ester (15)

$^1$H NMR (400 MHz, CDCl$_3$) δ 6.89 (dd, J=15.1, 10.7 Hz, 1H), 6.84 (d, J=14.7 Hz, 1H), 6.75 (s, 1H), 6.71 (dd, J=15.2, 10.7 Hz, 1H), 6.60 (d, J=15.4 Hz, 1H), 5.17 (t, J=9.3 Hz, 1H), 3.83 (s, 3H), 3.61 (dd, J=11.0, 9.3 Hz, 1H), 3.54 (dd, J=11.0, 9.3 Hz, 1H), 2.99 (s, 6H)

$^{13}$C NMR (101 MHz, CDCl$_3$) δ 171.4, 170.0, 156.5, 150.2, 141.7, 131.8, 127.1, 125.5, 120.8, 78.1, 53.0, 43.4×2, 34.8

HR-MS: m/z: [M+H]$^+$ calculated for $C_{14}H_{18}N_3O_2S_2$: 324.0840; measured: 324.0831

Synthesis of (S)-2-((1E,3E)-4-(5-(dimethylamino)thiazol-2-yl)buta-1,3-dien-1-yl)-4,5-dihydrothiazole-4-carboxylic acid (1-2)

(S)-2-((1E,3E)-4-(5-(Dimethylamino)thiazol-2-yl)buta-1,3-dien-1-yl)-4,5-dihydrothiazole-4-carboxylic acid methyl ester (15) (140 mg, 434 µmol) was suspended in ultrapure water (5 mL), 6 M HCl (5 mL) was added thereto, and then this solution was stirred at room temperature for 16 hours. The reaction mixture was neutralized through addition of sodium bicarbonate and was subsequently concentrated under reduced pressure. The resultant residue was purified by automated flash column chromatography (Smart Flash EPCLC AI-580S, ULTRAPACK COLUMNS $C_{18}$, H$_2$O/CH$_3$CN=9/1→1/9) to yield (S)-2-((1E,3E)-4-(5-(dimethylamino)thiazol-2-yl)buta-1,3-dien-1-yl)-4,5-dihydrothiazole-4-carboxylic acid (1-2) (115 mg, 371 µmol, 85%) as a yellow solid.

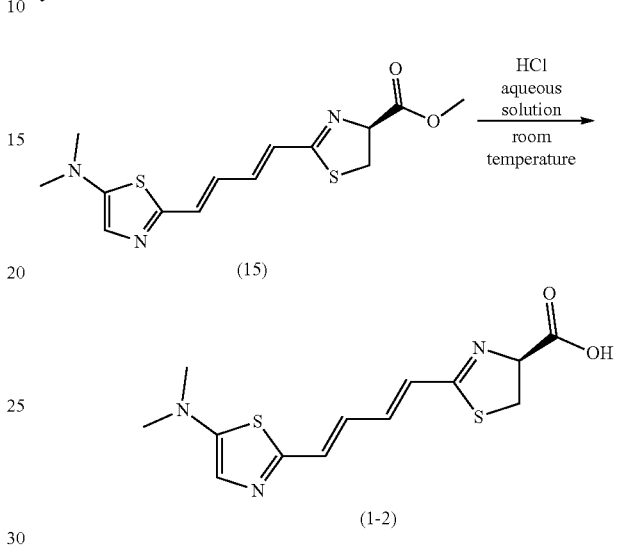

Results of identification of (S)-2-((1E,3E)-4-(5-(dimethylamino)thiazol-2-yl)buta-1,3-dien-1-yl)-4,5-dihydrothiazole-4-carboxylic acid (1-2)

$^1$H NMR (400 MHz, D$_2$O) δ 6.97 (td, J=15.2, 5.0 Hz, 1H), 6.84-6.81 (m, 3H), 6.59 (d, J=15.2 Hz, 1H), 5.03 (t, J=8.6 Hz, 1H), 3.65 (dd, J=11.3, 9.3 Hz, 1H), 3.45 (dd, J=11.0, 7.8 Hz, 1H), 2.95 (s, 6H)

$^{13}$C NMR (126 MHz, DMSO-d$_6$) δ 171.5, 162.7, 156.0, 149.1, 139.0, 130.2, 127.4, 126.9, 120.4, 83.3, 42.9×2, 35.5

HR-MS: m/z: [M+H]$^+$ calculated for $C_{13}H_{16}N_3O_2S_2$: 310.0684; measured: 310.0680

<Luminescence Spectrum Measurement>

The luminescent substrates represented by structural formulae (1-1) and (1-2) that were synthesized as described above, a luminescent substrate represented by the following structural formula (b), and natural firefly luciferin (LH$_2$, produced by Wako Pure Chemical Industries, Ltd.) represented by the following structural formula (d) were each used to measure a luminescence spectrum. Note that the luminescent substrate represented by structural formula (b) was prepared in accordance with Example 1 of JP2014-218456A (PTL 2).

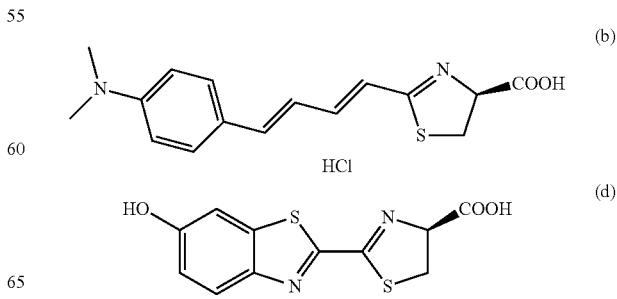

<<Measurement Apparatus>>
Luminescence Spectrum Measurement

A weak emission fluorescence spectrometer AB-1850 produced by ATTO Corporation was used to measure a luminescence spectrum. Each measured spectrum is a spectrum that has been corrected for detector characteristics (data interval 0.25 nm, measurement range 400 nm to 750 nm).

pH Measurement

An F-23 glass electrode hydrogen ion concentration indicator produced by Horiba, Ltd. was used to perform pH measurement.

<<Reagents>>
Ultrapure Water

Water taken from a Milli-RX 12α produced by Millipore Corporation

Ppy Luciferase (Derived from North American Firefly *Photinus pyralis*) Solution Recombinant luciferase (QuantiLum® (QuantiLum is a registered trademark in Japan, other countries, or both), catalogue no. E1701) produced by Promega Corporation ATP-Mg Solution Produced by Sigma (catalogue no. 00386-41)

Potassium Phosphate Buffer Solution (KPB Solution)

Dipotassium hydrogen phosphate dodecahydrate (special grade) and potassium dihydrogen phosphate dihydrate (special grade) produced by Wako Pure Chemical Industries, Ltd. dissolved in ultrapure water and pH adjusted <<Measurement Method>>

After mixing 5 μL of KPB solution (pH 8.0, 500 mM), 5 μL of luminescent substrate solution (100 μM), 5 μL of 1 mg/mL Ppy luciferase solution, and 10 μL of 200 μM ATP-Mg solution at room temperature, luminescence spectrum measurement was performed for 180 seconds using the luminescence spectrum measurement apparatus (AB-1850). The luminescence intensity was compared by the peak top value at this time. The results are illustrated in FIG. 1 and FIG. 2.

Figure 2:
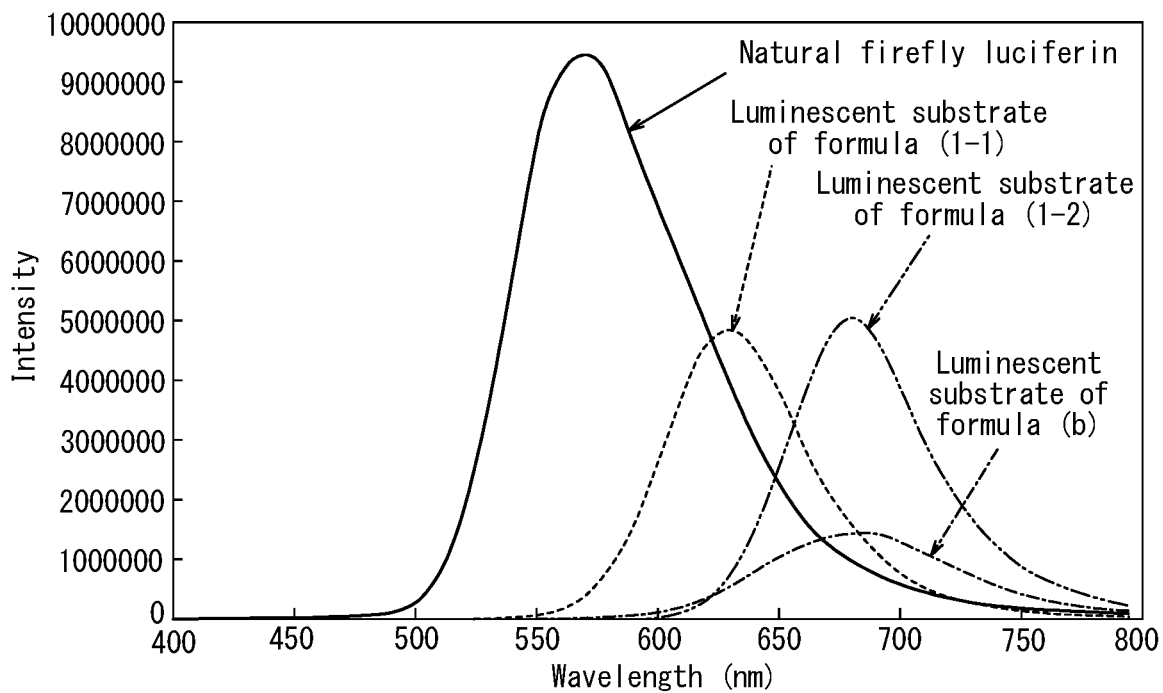
FIG. 2 is a luminescence spectrum illustrating luminescence intensity at each wavelength for luminescence systems in which a compound represented by structural formula (1-1), a compound represented by structural formula (1-2), a compound represented by structural formula (b), and natural firefly luciferin are respectively used as luminescent substrates.

FIG. 1 is a luminescence spectrum normalized to give a maximum value for luminescence intensity of 1, and FIG. 2 is a luminescence spectrum illustrating luminescence intensity at each wavelength.

<<Results>>

It can be seen from FIG. 1 that the luminescent substrate represented by structural formula (1-1) has a peak top wavelength of approximately 630 nm and that the luminescent substrate represented by structural formula (1-2) has a peak top wavelength of approximately 680 nm.

It can also be seen from FIGS. 1 and 2 that although the luminescence intensity of the luminescent substrate represented by structural formula (1-1) and the luminescent substrate represented by structural formula (1-2) is approximately half of that of natural firefly luciferin, these luminescent substrates can emit light with a long wavelength exceeding 600 nm and are effective for visualization of deep tissue.

Moreover, it can be seen that although the luminescent substrate represented by structural formula (1-1) has a shorter wavelength than the luminescent substrate represented by structural formula (b), the luminescence intensity of the luminescent substrate represented by structural formula (1-1) is approximately four times higher. Therefore, the luminescent substrate represented by structural formula (1-1) is effective for visualization of deep tissue because, even though absorption of light by biological substances increases due to the shorter wavelength, the luminescence intensity is significantly higher and the amount of light that permeates from deep tissue is greater (i.e., because the effect of increased luminescence intensity is greater than that of increased light absorption).

Furthermore, it can be seen that the luminescent substrate represented by structural formula (1-2) is particularly effective for visualization of deep tissue because it has a similar wavelength to the luminescent substrate represented by structural formula (b) while also having a luminescence intensity that is approximately four times higher, and thus the amount of light that permeates from deep tissue is significantly greater.

INDUSTRIAL APPLICABILITY

The heterocyclic compound and salt thereof according to the present disclosure can be used as a luminescent substrate in a firefly bioluminescence system.

The invention claimed is:

1. A heterocyclic compound of formula (1):

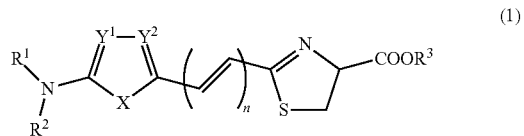

where $R^1$, $R^2$, and $R^3$ are each independently hydrogen or an alkyl group having a carbon number of 1 to 4, with provisos that $R^1$ and $R^2$ are optionally bonded to each other to form a ring and that one of $R^1$ and $R^2$ is optionally bonded to $Y^1$ to form a ring, X is S, O, $NR^4$, or $CH_2$, and $Y^1$ and $Y^2$ are each independently N or $CR^4$, where each $R^4$ is independently hydrogen, an alkyl group having a carbon number of 1 to 4, an alkenyl group having a carbon number of 2 to 4, or an acyl group having a carbon number of 2 to 4, and n is an integer of 0 to 4.

2. The heterocyclic compound according to claim 1, wherein either or both of $Y^1$ and $Y^2$ are N.

3. The heterocyclic compound according to claim 1, wherein X is S.

4. The heterocyclic compound according to claim 1, represented by the following structural formula (1-1) or (1-2):

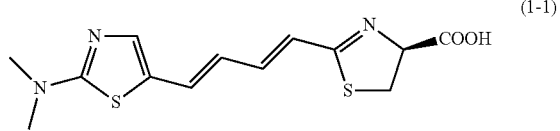

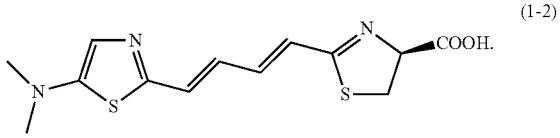

5. A salt of the heterocyclic compound according to claim 1.

6. A luminescent substrate composition comprising the heterocyclic compound according to claim 1.

7. The heterocyclic compound according to claim 2, wherein X is S.

8. The heterocyclic compound according to claim 2, represented by the following structural formula (1-1) or (1-2):

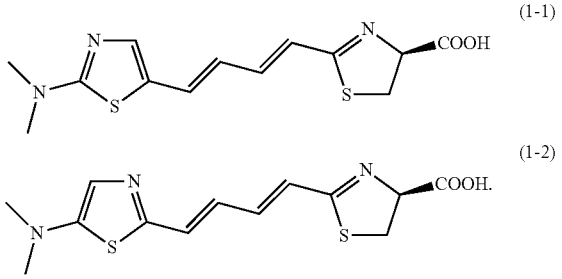

9. A salt of the heterocyclic compound according to claim 2.

10. A luminescent substrate composition comprising the heterocyclic compound according to claim 2.

11. The heterocyclic compound according to claim 3, represented by the following structural formula (1-1) or (1-2):

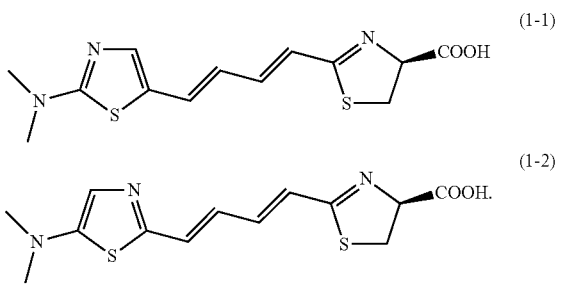

12. A salt of the heterocyclic compound according to claim 3.

13. A luminescent substrate composition comprising the heterocyclic compound according to claim 3.

14. A salt of the heterocyclic compound according to claim 4.

15. A luminescent substrate composition comprising the heterocyclic compound according to claim 4.

16. A luminescent substrate composition comprising the salt according to claim 5.

17. The heterocyclic compound according to claim 7, represented by the following structural formula (1-1) or (1-2):

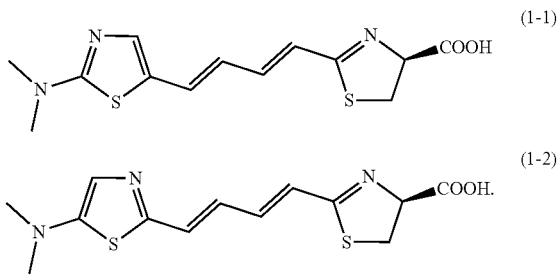

18. A salt of the heterocyclic compound according to claim 7.

19. A luminescent substrate composition comprising the heterocyclic compound according to claim 7.

20. A salt of the heterocyclic compound according to claim 8.

* * * * *